(12) United States Patent
Kiraly et al.

(10) Patent No.: US 6,880,952 B2
(45) Date of Patent: Apr. 19, 2005

(54) EXTENSIBLE LINEAR LIGHT EMITTING DIODE ILLUMINATION SOURCE

(75) Inventors: Chris Kiraly, San Diego, CA (US); Gene Henke, San Diego, CA (US)

(73) Assignee: Wintriss Engineering Corporation, San Diego, CA (US)

( * ) Notice: Subject to any disclaimer, the term of this patent is extended or adjusted under 35 U.S.C. 154(b) by 48 days.

(21) Appl. No.: 10/391,888

(22) Filed: Mar. 18, 2003

(65) Prior Publication Data

US 2003/0174517 A1 Sep. 18, 2003

Related U.S. Application Data (60) Provisional application No. 60/366,066, filed on Mar. 18, 2002.

(51) Int. Cl.$^7$ ................................................ F21V 7/20
(52) U.S. Cl. ........................ 362/218; 362/221; 362/223; 362/294; 362/373; 362/545; 362/800; 348/131; 382/141
(58) Field of Search ................................ 362/545, 241, 362/247, 294, 373, 218, 219, 221, 223, 800, 11, 267; 348/131; 382/141

(56) References Cited

U.S. PATENT DOCUMENTS

| | | | | |
|---|---|---|---|---|
| 5,490,048 A | * | 2/1996 | Brassier et al. | 362/238 |
| 5,499,170 A | * | 3/1996 | Gagne | 362/84 |
| 5,657,159 A | * | 8/1997 | Natori | 359/448 |
| 6,450,664 B1 | | 9/2002 | Kelly | |
| 6,472,823 B2 | * | 10/2002 | Yen | 315/112 |
| 6,561,690 B2 | * | 5/2003 | Balestriero et al. | 362/555 |
| 6,641,284 B2 | * | 11/2003 | Stopa et al. | 362/240 |
| 6,659,622 B2 | * | 12/2003 | Katogi et al. | 362/219 |
| 6,659,623 B2 | * | 12/2003 | Friend | 362/249 |
| 6,739,735 B2 | * | 5/2004 | Talamo et al. | 362/249 |
| 2002/0036908 A1 | * | 3/2002 | Pederson | 362/545 |
| 2002/0196623 A1 | * | 12/2002 | Yen | 362/245 |

OTHER PUBLICATIONS

Data sheet, Illumination Technologies, 2001, 2 pages.
Data sheet, Volpi Manufacturing USA, published on website (address at http://volpiusa.com/machinevision/data_sheet/led_lightline.html), downloaded on Mar. 15, 2002, 1 page.
Data sheet, Laser optronix, published on website (address at http://laseroptronix.com/led/broms.html), downloaded on Mar. 15, 2002, 2 pages.
Data sheet, StockerYale (IRL), Ltd., 2001, 2 pages.

* cited by examiner

*Primary Examiner*—Thomas M. Sember
*Assistant Examiner*—Jacob Y. Choi (57) ABSTRACT

A compact, energy-efficient extensible illumination source combines the reliability advantages of light emitting diodes (LEDs) with the brightness of conventional lighting. High reliability of the LEDs provides trouble-free operation over a long hour lifetime. This high-output light source can be used in direct lighting applications or for backlighting for translucent materials. The illumination source includes LED printed wire board segments that may be configured to form a light line of any length. The segments are mounted on a inner mounting base which also serves as a first stage heat sink for the LEDs. The illumination source includes a linear mirror for reflecting radiant energy away from the LEDs to produce a uniform linear illumination pattern. A window provides mechanical protection for the LEDs and may be used for diffusing or filtering light from the LEDs. An integral base in contact with the inner mounting base also serves as a heat sink and provides structural support for the illumination source. The integral base further includes channels and cavities for cooling the illumination source and for housing power cables.

21 Claims, 6 Drawing Sheets

EXTENSIBLE LINEAR LIGHT EMITTING DIODE ILLUMINATION SOURCE

RELATED APPLICATIONS

This application claims the benefit of priority under 35 U.S.C. 119(e) to provisional U.S. patent application Ser. No. 60/366,066, filed Mar. 18, 2002 which is incorporated herein by reference in its entirety.

FIELD OF THE INVENTION

This invention relates generally to linear light sources, and more specifically to an assembly of high-intensity light emitting diodes in a linear, modular form such that the illumination line can be extended indefinitely.

BACKGROUND OF THE INVENTION

Linear light arrays are desirable for use when an specific long, narrow target area must be illuminated. One such use is for illumination of a continuous web in a web manufacturing inspection system. A web is any material which is manufactured in a single continuous sheet, such as paper and cloth. The web typically passes through a web inspection station that analyzes the web for defects. Cameras are positioned along the width of a web, with each camera taking images of a specific portion of the width of the web. Defects in the web, including discolorations, holes and tears, are identified as inconsistences in the images. Thus, the analysis depends upon consistent lighting of the web. Although the analysis may correct for minor lighting variations, dark spots caused by defective or inconsistent lighting may result in a false identifications of defects.

A number of companies manufacture modular LED linear arrays. However, these LED linear arrays often are of a fixed length that are not sufficiently long to illuminate a target width. Linear arrays that are extensible use modules that, when connected together, result in gaps between the modules so that the illumination is not uniform. In addition, the brightness of the existing illumination arrays are limited, and the focus of the light is not controllable. Some product offerings consist of LED circuit cards only, requiring the end user to construct a housing, structural mountings, and cooling provisions. Typical prior art illumination sources do not provide sufficient provisions for heat flow away from the illumination source. In addition, these products do not have power supply distribution provisions, and are not sealed for use in extreme environments.

Therefore, a need exists for an illumination source which is compact, energy-efficient and indefinitely extensible, and which combines the reliability advantages of light emitting diodes (LEDs) with the brightness of conventional lighting for use in direct lighting applications or for backlighting for translucent materials. A need exists for an illumination source that includes LED printed wire board segments that are mountable on an inner mounting base, wherein the LED printed wire board segments are configured to form a uniform illumination line of any length. A further need exists of an illumination source that includes an integral base in contact with the inner mounting base which serves as a heat sink and provides structural support for the illumination source, and which includes channels and cavities for cooling the illumination source and for housing power cables.

SUMMARY OF THE INVENTION

It is an advantage of the present invention to provide an illumination source that utilizes an illumination elements, e.g, light emitting diodes, to provide maximum brightness, long life, and diffuse or focused light of various wavelengths.

It is a further advantage to provide an illumination source that is extensible to any length while providing uniformity of illumination.

If is another advantage to provide an illumination source that individually groups LEDs to avoid catastrophic failure of the entire linear LED array.

Another advantage of the present invention is to provide an illumination source that has a power distribution system that provides equal power to each LED of the linear LED array.

Yet another advantage is to provide an environmentally sealed illumination source having structural supports which act as heat sinks, include cooling channels for forced air and other cooling means, and provide flexible mounting provisions.

The exemplary embodiment of the present invention is a compact, energy-efficient extensible illumination source that utilizes light emitting diodes (LEDs) to provide the advantages of brightness and high reliability. The high reliability of the LEDs provides trouble-free operation over a long hour lifetime. The illumination source of the exemplary embodiment includes LED printed wire board segments that may be configured to form a light line of any length. The segments are mounted on a inner mounting base which also serves as a first stage heat sink for the LEDs. Linear mirrors are mounted on the inner mounting base with the LEDs running lengthwise between the mirrors. The mirrors reflect and focus the radiant energy from the LEDs onto the target to produce a uniform linear illumination pattern. A window is mounted in the illumination source above the LEDs and mirrors to provide mechanical protection for the LEDs. The window may be used for diffusing or filtering light from the LEDs.

Many applications require continuous, high intensity linear light sources of indefinite length. The exemplary embodiment of the illumination source includes assembled segments of a length which can be practically manufactured, and which include provisions for joining individual assemblies together to make indefinitely extensible linear light sources. In one embodiment of the invention, the mounting base and printed wire boards form an assembled segment with the LEDs mounted in patterns such that when these segments are combined, end to end, the illumination remains uniform over the length of the combined assemblies. The assembled segments are mounted on a base and enclosed by brackets to provide an environmental seal as well as structural integrity for the illumination source unit. Each assembled segment of the exemplary embodiment is powered individually by cables so as to avoid power distribution problems.

In the exemplary embodiment of the present invention, provisions are made to carry away the heat generated by the LEDs to surrounding structures. For example, the high intensity light emitting diodes (LEDs) are secured to the mounting base with heat conducting adhesives. The mounting base thus acts as a heat sink member. An integral base in contact with the inner mounting base also serves as a heat sink and provides structural support for the illumination source. The integral base further includes channels and cavities for cooling the illumination source and for housing power cables.

In other embodiments of the invention, the high intensity linear light source may be shaped in other geometries other than a straight line, e.g., circular, by designing the printed circuit board accordingly. The light source of alternate embodiments can be lasers or incandescent lamps. In addition, the circuits controlling the light source can be designed to strobe the light source.

The extensible linear light emitting diode illumination source of an exemplary embodiment is utilized in web inspection systems. The illumination source illuminates the continuously manufactured materials, i.e., "webs", that are under inspection. The web inspection systems utilize cameras which optically inspect the webs for surface and other defects. Identified defect areas are analyzed by the cameras and/or by computers which receive the defect information from the cameras. Typical applications of the web inspection system includes defect detection of metals, non-woven materials, textiles, fabrics, film, paper, plastics and other materials that are manufactured as continuous web sheets. The illumination source of the exemplary embodiment provides uniform lighting of the web which enables the cameras and/or computers to accurately inspect the webs.

BRIEF DESCRIPTION OF THE DRAWINGS

The present invention will be better understood from the accompanying drawings in which.

DESCRIPTION OF THE PREFERRED EMBODIMENT

Figure 1:
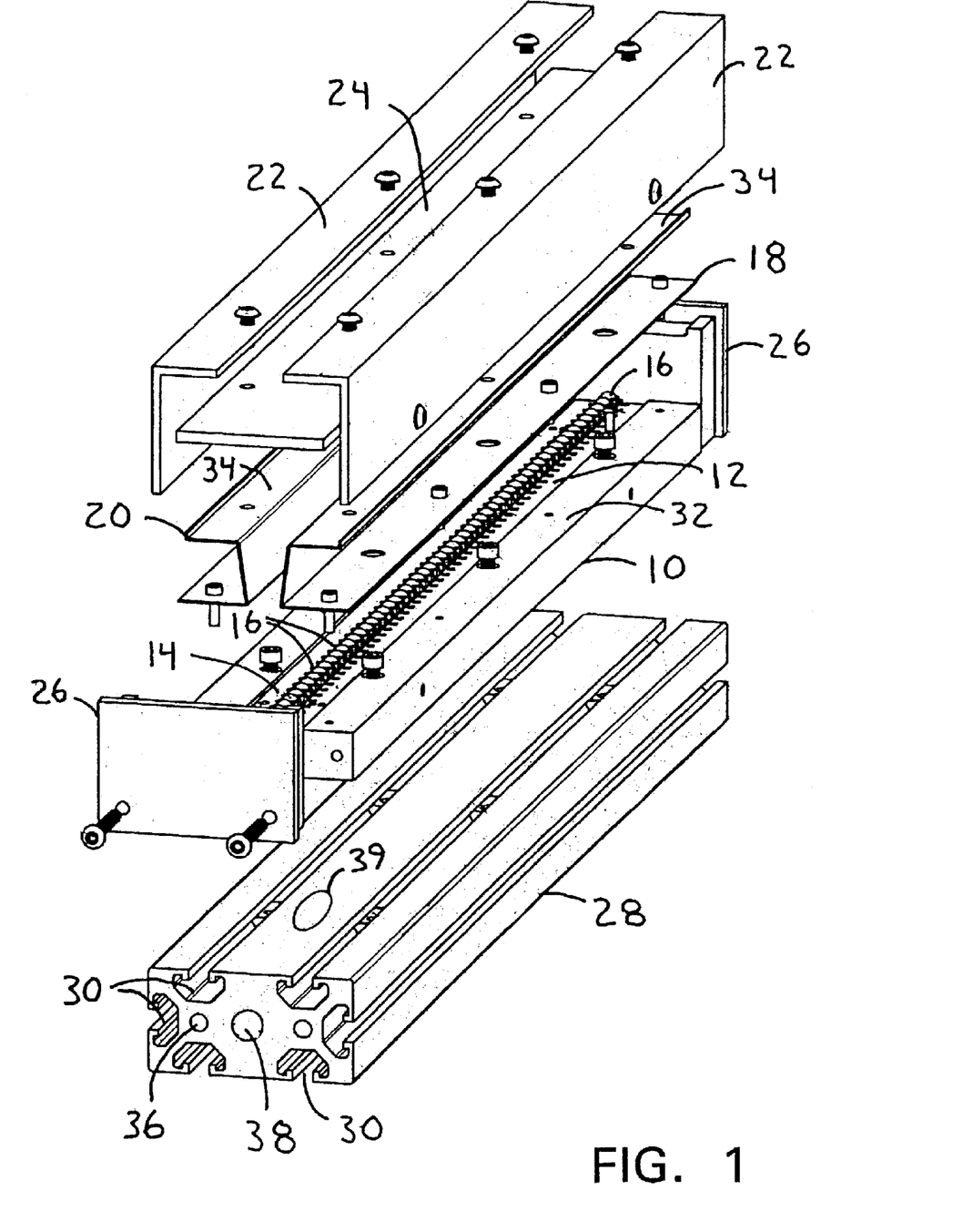
FIG. 1 is an exploded top view of an assembly of an extensible linear light emitting diode illumination source of a preferred embodiment of the present invention.
Figure 3:
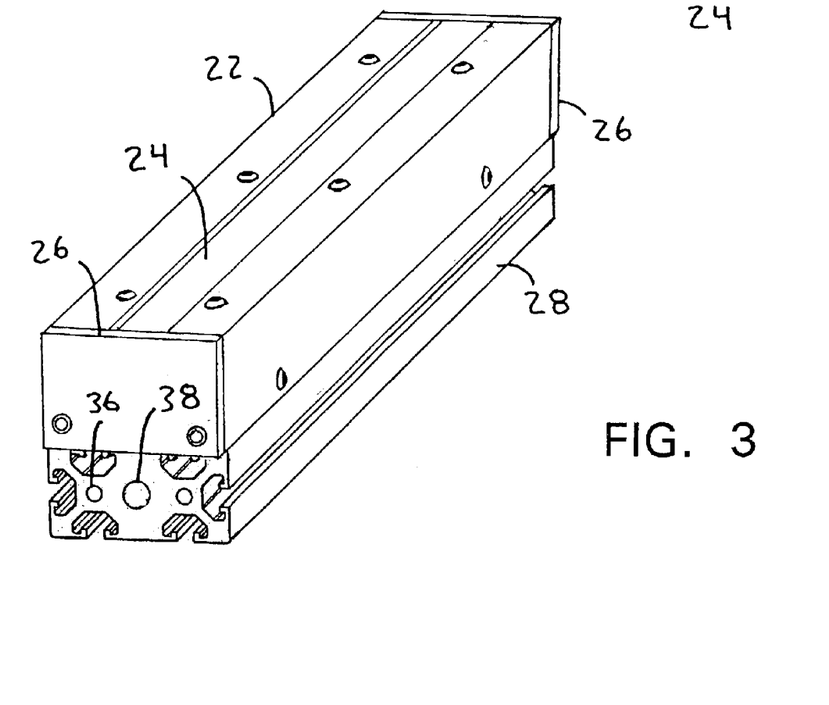
FIG. 3 is a isometric view of an assembled extensible linear light emitting diode illumination source.
Figure 11:
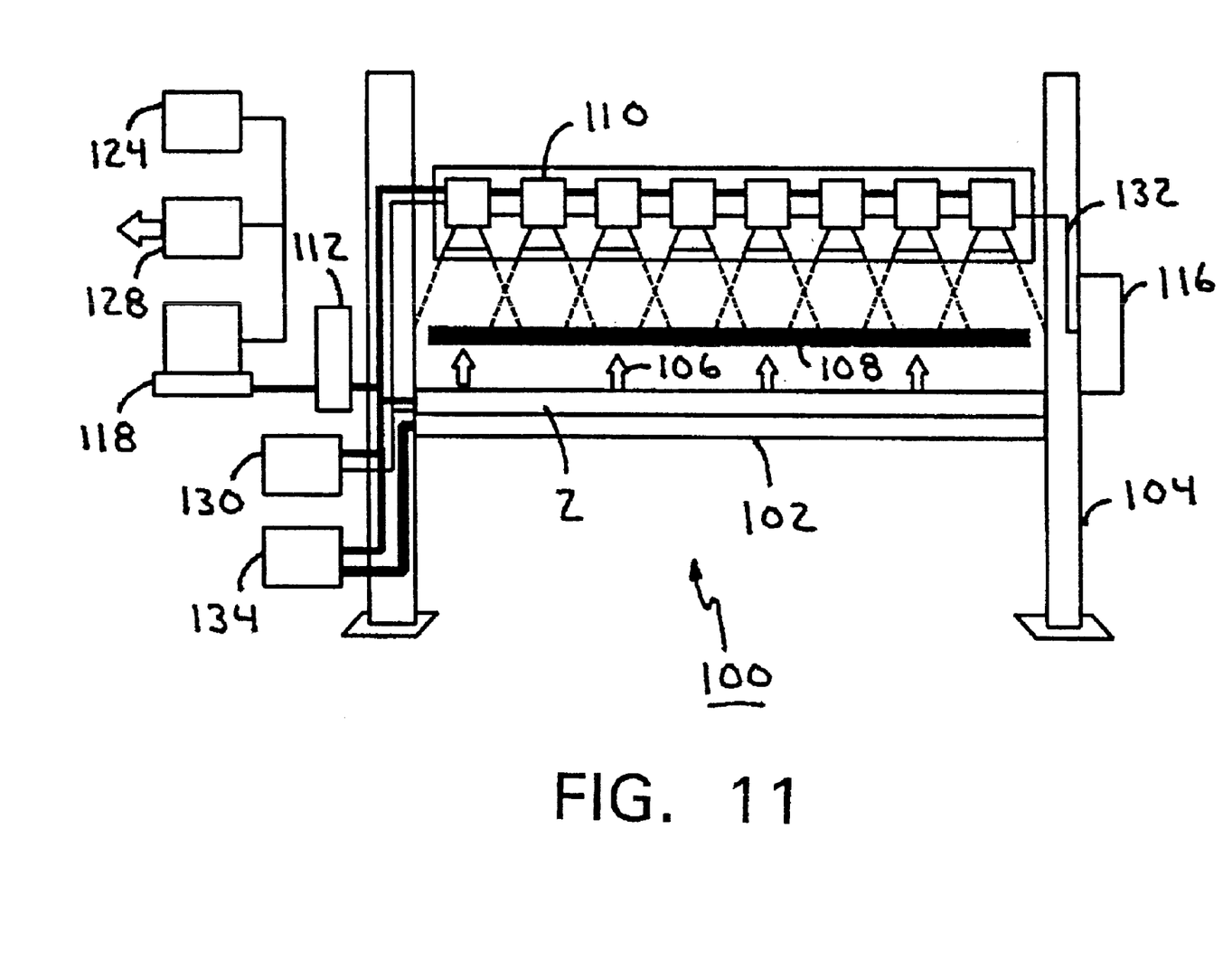
FIG. 11 is a drawing of a web inspection system utilizing the extensible linear light emitting diode illumination source of a preferred embodiment.

FIG. 1 illustrates an exploded view of an assembly of an extensible linear light emitting diode illumination source of a preferred embodiment of the present invention, while FIG. 3 illustrates the assembled illumination source and FIG. 11 illustrates a web inspection system utilizing the extensible linear light emitting diode illumination source 2. The illumination source 2 includes an inner printed wire board (PWB) mounting base 10 attached to a base 28. Right and left mirrored window supports 18, 20 are mounted to a top surface 32 of the PWB mounting base 10. A window 24 is mounted to top surfaces 34 of the window supports 18, 20. The PWB mounting base 10, the mirrored window supports 18, 20, and the window 24 are enclosed by brackets 22 and end caps 26. The brackets 22, end caps 26, base 28 and window 24 create an environmentally sealed assembly 2.

Figures 4, 5, 6:
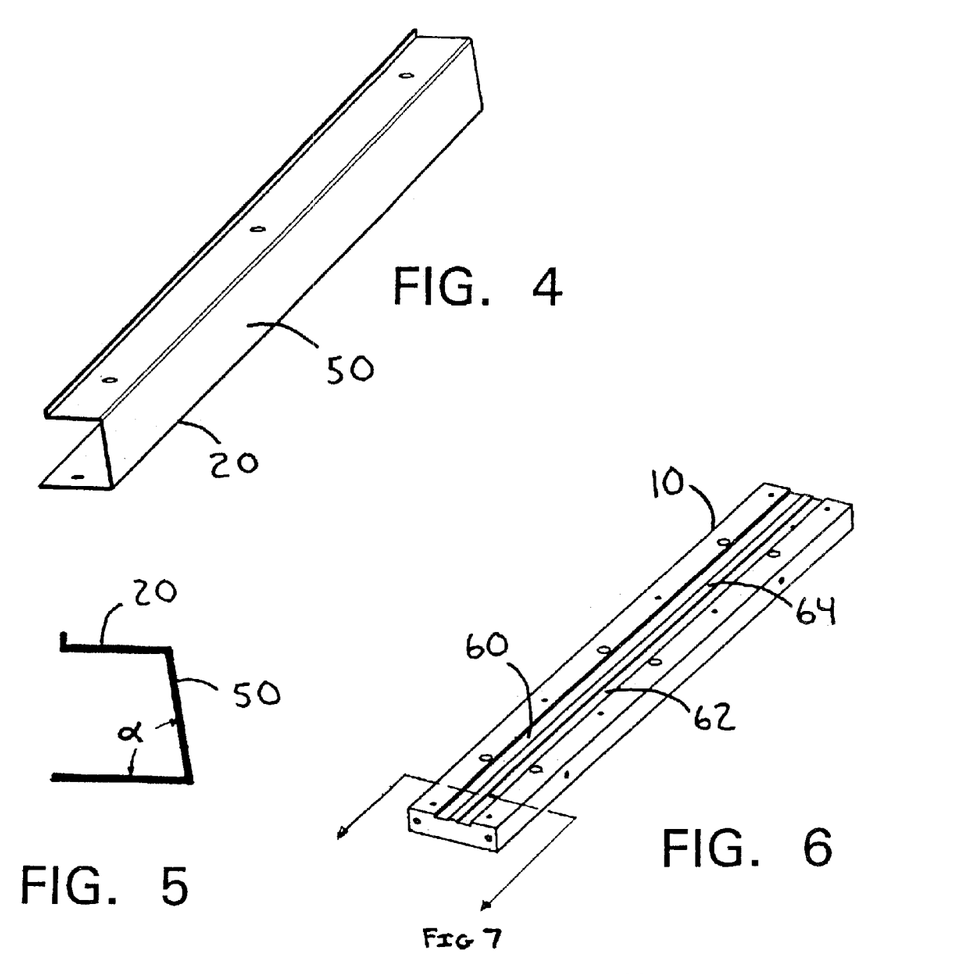
FIG. 4 is a isometric view of a mirrored window support of a preferred embodiment of the present invention.
FIG. 5 is an side view of the mirrored window support illustrating an angle of the mirror surface.
FIG. 6 is a isometric view of an inner Printed Wire Board (PWB) mounting base of an extensible linear light emitting diode illumination source of the present invention.
Figure 7:
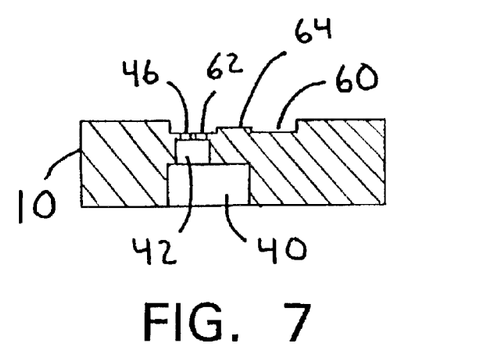
FIG. 7 is a cross sectional view of the inner PWB mounting base of FIGS. 6 and 9.
Figures 9, 10:
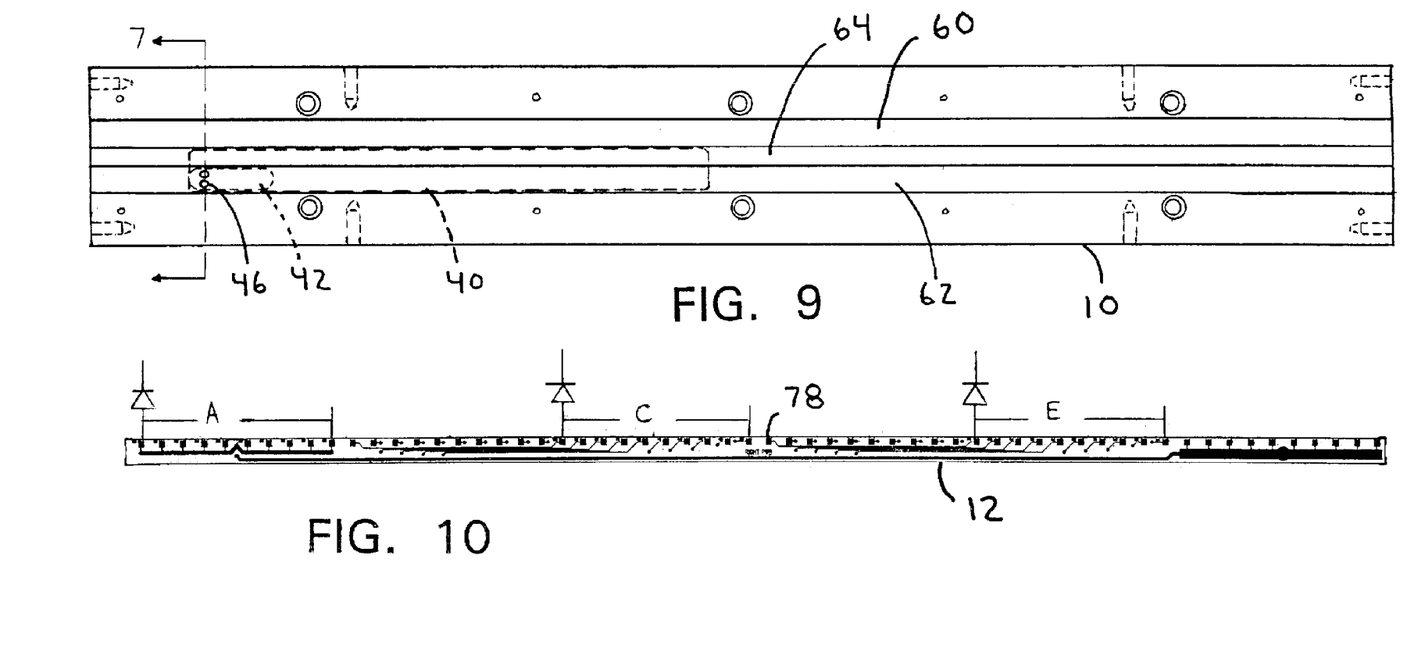
FIG. 9 is a top view of an inner mounting base of a preferred embodiment.
FIG. 10 is a drawing of a top layer of a right PWB of the present invention.

Continuing with FIG. 1, the illumination source 2 includes light emitting diodes (LEDs) 16, which are positioned along an entire length of the inner PWB mounting base 10. As shown in FIGS. 6, 7, and 9, the PWB mounting base 10 includes left and right troughs 60, 62 for accepting and securing the right and left PWB segments 12, 14. One of the cathode or anode leads of each LED is mounted on a right LED printed wire board (PWB) segment 12, and the other of the cathode or anode leads of each LED are mounted on a left LED PWB segment 14. The illumination source 2 in alternate embodiments utilizes incandescent light, lasers, or other illumination sources in place of the LEDs 16.

Figure 8:
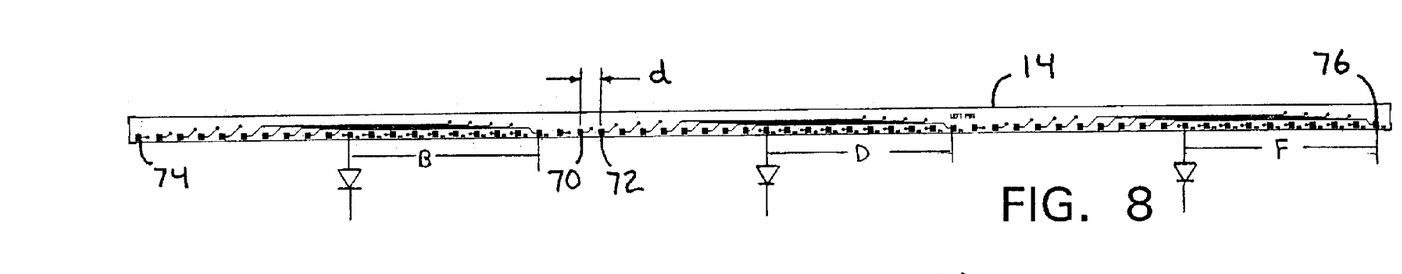
FIG. 8 is a drawing of a top layer of a left PWB of an embodiment of the present invention.

Each PWB segment 12, 14 may be of a standardized size that has lead pads spaced evenly along the entire length of the segment. In other embodiments of the invention, the lead pads may be configured in other patterns to produce light patterns that are required by specific applications of the illumination source 2. FIGS. 8 and 10 illustrate left and right PWB segments 12, 14 of a preferred embodiment with lead pads 70, 72, 74, 76, 78. The distance "d" between each lead pad 70, 72 is constant. Further, a distance between the first lead pad 74 and the leading edge of the PWB 12, 14, and the last lead pad 76 and the trailing edge of the PWB 12, 14 joined together equal the constant distance "d". Thus, the illumination source 2 is extensible by joining right and left segments 12, 14 end to end. The resulting illumination source 2 produces a uniform illumination, i.e., without illumination gaps, along its entire length.

All linear components, including the base 30, the PWB mounting base 10, the mirrored window supports 18, 20, the window 24 and the brackets 22, as shown in FIG. 1, can be manufactured to be of a particular length corresponding to the total number of end to end PWB segments 12, 14 required for a specific application of the illumination source 2. In a preferred embodiment of the invention, only the printed wiring boards 12, 14 are manufactured and assembled in short 20 inch (50.8 cm) segments. Continuous length linear components, as described above, provide for mechanical integrity of the resulting illumination source assembly 2. However, in alternate embodiments of the invention, a grouping of assembled components can create an assembled segment that is held together by brackets 24 and/or a base 30 of the required application length, as long as the grouping of assembled components maintain mechanical integrity and an environmental seal.

Referring to FIGS. 6, 7, and 9, the LED printed wire boards 12, 14 are securely fastened to the inner mounting base 10 which provides a heat sink path for dissipating heat generated by the LEDs 16. The right and left PWB segments 12, 14 are positioned such that the LEDs 16 straddle a center ridge 64 of the mounting base 10. The center ridge 64 of a preferred embodiment acts as a continuous structural support member and efficient heat sink for the LEDs 16. The LEDs 16 are placed in intimate contact with the center ridge 64 of the inner mounting base 10. In a preferred embodiment of the invention, the LEDs 16 are cemented to the center ridge 64 using conductive cement to increase rigidity of the LEDs as well as to provide maximum heat transfer of the heat generated by the individual LEDs to the inner mounting base 10.

Figure 2:
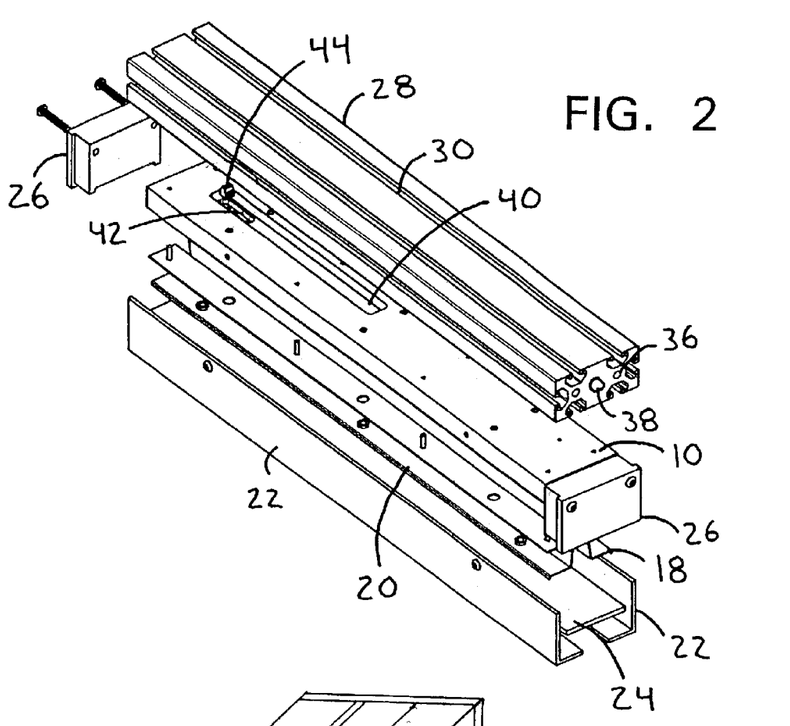
FIG. 2 an exploded bottom view of the assembly of FIG. 1.

As shown in FIGS. 1, 2, and 3, the inner PWB mounting base 10 is in intimate contact with an outer support structure and base 28 which provides a further path for heat transfer. A base 28 of a preferred embodiment is extruded aluminum for maximum heat dissipation. Linear cavities 36 in the base 28 provide for the circulation of cooling fluid as necessary. Fans, filters and electrical junction boxes 130, 134, as shown in FIG. 11, can be attached at each terminus of the base 28 to force cooling air through the linear cavities 36, and/or the cable conduits 38 in the base 28. Mounting channels 30 are utilized for mounting the entire assembly 2 to a supporting structure 102, as illustrated in FIG. 11. The cable conduits 38 are used for running electrical and power supply cables to each of the PWB segments 12, 14.

FIG. 2 illustrates an exploded bottom view of the extensible linear light emitting diode illumination source 2 of FIG. 1. Although for discussion purposes FIG. 2 is referred to as a bottom view, it should be appreciated that the illumination source may be mounted above or in front of a target to provide top or front lighting, or may be mounted below or behind the target to provide backlighting. The lighting configuration and type of LED utilized depends upon the application of the illumination source. For example, in a web defect detection system 100, as shown in FIG. 11, the material and type of defects to be detected dictates the lighting configuration, including the configurations of backlighting, front diffuse lighting, front specular lighting, dark field lighting, and oblique lighting.

Continuing with FIG. 2, the bottom surface of the inner PWB mounting base 10 includes an electrical inset 40 that is aligned with a bore or hole 39 in the base 28. A terminal block slot 42 is recessed within the electrical inset 40 for housing a terminal block 44. The terminal block 44 connects power supply wiring to the PWB segment 12, 14 via feed thru slots 46, as shown in FIGS. 7 and 9. In the preferred embodiment each LED illumination segment 12, 14 has is own power supply connection which allows the LED illumination source 2 to be extended indefinitely without undue power variations between LED illumination segments 12, 14.

The light emitting diodes of a preferred embodiment are red LEDs having a light output of 75,000 Lux. Red LEDs provide maximum illumination while providing a long lifetime, e.g., 100,000 hours. An illumination source of a preferred embodiment of the invention requires a 17V DC power source, at 3.5 amps per PWB segment 12, 14. In alternate embodiments of the invention, other color wavelength LEDs, or other radiant sources of any wavelength colors, may be utilized if the application so requires. The use of LEDs in the illumination source provides illumination uniformity within 10% or better along the entire length of the illuminated target. In addition, the use of LEDs 16 in conjunction with the window 24 and mirror 50, as described further below, provides a highly controllable and directed light output.

The window 24 of a preferred embodiment, as shown in FIGS. 1 and 2, provides for mechanical protection for the LEDs 16. The type of window 24 utilized in the illumination source 2 may vary according to the intended use of the illumination source 2. For example, a translucent window 24 may be used as a diffuser in situations where diffused illumination is required. A clear window 24 may be used for non-diffuse applications. A specific color window 24 may be utilized when filtered emissions are appropriate. Other windows 24 may utilize lenslets, or continuous cylindrical or other shaped lenses, to focus the light from the illumination source, e.g., the LEDs 16.

FIGS. 1 and 4 illustrate mirrored window supports 18, 20 of a preferred embodiment. The mirror-finished surface 50 of the window support 18, 20 serves to reflect radiant energy from the individual LEDs 16 in such a manner that a maximum amount of radiant energy is directed away from the LED illumination source 2 and towards the intended target such as a web 108, as shown in FIG. 11. The LEDs 16 are centered between the right mirrored window support 18 and the left mirrored window support 20. The mirrors 50 span the entire length of the LED illumination source 2 to provide a continuous, uniform, linear illumination.

FIG. 5 is an end view of the mirrored window support 18, 20. As illustrated in FIG. 5, the mirrored surface 50 is angled with respect to the plane of the PWB segments 12, 14 on which the mirrored window supports 18, 20 are anchored. The mirrored surface 50 outwardly reflects the illumination produced by the LEDs 16. In the preferred embodiment of the invention, the inside angle $\alpha$ of the bracket is approximately 80 degrees, to optimize the illumination intensity since LEDs typically emit a wide angle of illumination. In other embodiments, the angle is varied depending upon the lighting conditions necessary for the specific lighting requirements of the illumination source 2.

FIGS. 8 and 10 illustrate the top layers of the left and right printed wiring boards segments 14, 12 of an embodiment of the invention. The left and right printed wiring board segments 14, 12 are utilized to attach the anode and cathode wiring leads of the individual LEDs 16. In the preferred embodiment, the printed wiring board circuitry/traces are arranged in a parallel series configuration so that the failure of a single component, e.g., an LED 16, does not result in the loss of significant radiated illumination. In the example illustrated in FIGS. 8 and 9, the bottom layers of the PWB segments 12, 14, not shown, include traces which connect groups of lead pads to create a series connection. For example, the cathodes of ten (10) LEDs of group A are connected in parallel on the right PWB 12, the anodes of these LEDs are connected in series to group B on the left PWB 14. The parallel series continues until the end of the PWD segments 12, 14, when the anodes of the LEDs of group F are connected to a power return. This configuration results in ten (10) parallel LED paths of six (6) LEDs each. Thus, if an LED 16 of a series fails resulting in the failure of the other five LEDs of the series, then the surrounding LEDs of the other series will provide sufficiently uniform illumination along the length of the illumination line.

Figure 12:
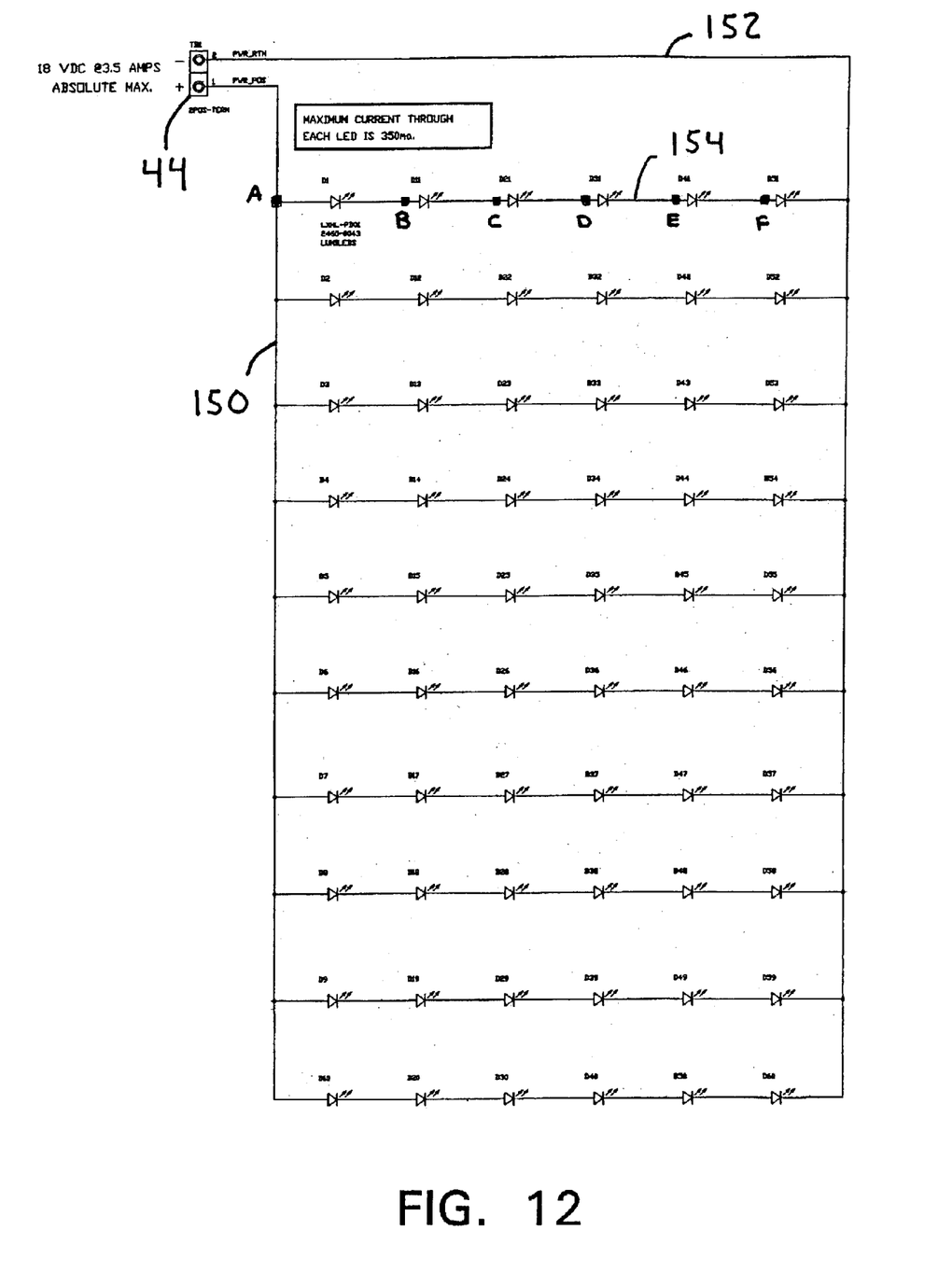
FIG. 12 is a schematic diagram of the circuit of a preferred embodiment of the invention.

FIG. 12 illustrates the circuit realized by the right and left PWB segments 12, 14 of FIGS. 8 and 10. Terminal block 44 includes a power line 150 connected to the cathodes of the ten LEDs of group A. Six LEDs are connected in ten (10) series branches 154. The anodes of the final LEDs in the series 154 branches are connected to the power return of the terminal block 44 via line 152.

The extensible linear light emitting diode illumination source 2 may be used for surface inspection applications. FIG. 11 illustrates a high performance, web inspection system 100. The system 100 utilizes smart linescan cameras 110 which optically inspect continuous materials 108, i.e., "webs", for surface defects. Typical applications of the web inspection system 100 includes defect detection of metals, non-woven materials, textiles, fabrics, film, paper, plastics and other materials that are manufactured as continuous web sheets. The system 100 employs digital filter processing, adaptive background subtraction and advanced software algorithms to detect very small changes in surface properties.

Continuing with FIG. 11, the web inspection system 100 includes an illumination source 2 of the preferred embodiment which directs light upward 106 towards the web 108. Thus, FIG. 11 illustrates a backlit web 108. In other embodiments of the web inspection system 100, the illumination source 2 may be position above the web 108 for top lighting. The illumination source 2, consisting of a number of PWB segments 12, 14, is mounted on a structural support member 102 by means of the channels 30 of the base 28, as described above. A structural support stand 104 supports both the bank of cameras 110 and the illumination source 102. The cameras 110, which are synchronized by an encoder 116 and synchronization signal 132, output defect results to a computer 118 by means of an ethernet hub 112. Power supplies 130 provide power to the cameras 110 and the illumination source 2. Cooling equipment 134 provides cooling to the illumination source 2. In a preferred embodiment of the invention, the computer 118 controls all elements of the inspection system 100, including the cameras 110, the illumination source 2, the power supply 130, and the cooling equipment 134. The inspection system 100 is also connected via a network to additional equipment such as a remote monitor 124 and a modem 128 that connects to, e.g., the Internet.

Although a preferred embodiment of the invention has been described above by way of example only, it will be understood by those skilled in the field that modifications may be made to the disclosed embodiment without departing from the scope of the invention, which is defined by the appended claims.

We claim:

1. An illumination source for illuminating a target, comprising:
    an elongate mounting base having opposite first and second surfaces and a heat sink extending along the length of the mountain base;
    at least one right printed wire board segment;
    at least one left printed wire board segment separate from said right printed wire board segment;
    a plurality of LEDs mounted at equally spaced intervals along said heat sink whereby heat transfer is provided from the LEDs to the mounting base, each LED of the plurality having a cathode lead attached to one of the at least one right printed wire board segment and the at least one left printed wire board segment, and each LED of the plurality having an anode lead attached to the other of the at least one right printed wire board segment and the at least one left printed wire board segment;
    a support base attachable to the second surface of the mounting base, the support base having a first length, the base constructed from a heat transferring material, the support base comprising a plurality of interior channels extending the first length;
    at least two support members attached to the first surface of the mounting base such that the plurality of LEDs are located therebetween, each of the at least two support members comprising a mirrored surface adjacent the plurality of LEDs for directing illumination produced by the plurality of LEDs towards the target;
    a window attached to the at least two support members; at least two brackets having the first length for enclosing the mounting base, the at least two support members, and at least a portion of the window; and
    at least two end caps for enclosing a first and second end of each of the at least two brackets.

2. The illumination source of claim 1, wherein at least one of the plurality of interior channels is utilized for cooling the illumination source.

3. The illumination source of claim 1, wherein the at least one of the plurality of channels is utilized for housing electrical wires, the electrical wires supplying power to the plurality of LEDs.

4. The illumination source of claim 1, wherein the at least one right printed wire board segment comprises a plurality of right printed wire board segments connected end-to-end, and the at least one left printed wire board segment comprises a plurality of left printed wire board segments connected end-to-end.

5. The illumination source of claim 1, wherein each of the mirrored surfaces of the at least two support members is angled to direct light from the plurality of LEDs in a first manner.

6. The illumination source of claim 1, wherein each of the at least one right and left printed wire board segments comprises a plurality of equidistantly-spaced lead pads for accepting the anode and cathode leads of the plurality of LEDs, wherein the illumination produced by the equidistantly-spaced LEDs is uniform over the target.

7. The illumination source of claim 1, wherein the equidistantly-spaced lead pads are connected in a parallel series configuration.

8. A method of illuminating a target having a width with a uniform illumination across the width of the target, the method comprising the steps of:
    mounting a right printed wire board segment and a left printed wire board segment on opposite sides of a heat sink on a mounting base;
    mounting a plurality of LEDs at equally spaced intervals along said heat sink, said LEDs having first and second leads to the right and left printed wire board segments, wherein the first lead of each LED of the plurality of LEDs is connected to one of the right and left printed wire board segments, and the second lead of each LED of the plurality of LEDs is connected to the other one of the right and left printed wire board segments;
    adhering the plurality of LEDs to the heat sink of the mounting base;
    attaching at least two window support means to the inner PWB mounting base, wherein the plurality of LEDs are positioned between the at least two window support means;
    attaching a window to the at least two window support means, the window positioned so that illumination from the LEDs passes through the window;
    mounting the mounting base to a support base; and
    enclosing the mounting base, the at least two window support means, and at least a portion of the window utilizing at least to two brackets.

9. The method of claim 8, further comprising the step of connecting the plurality of LEDs in a parallel series configuration.

10. The method of claim 8, further comprising the steps of:
    providing at least one cooling channel in the support base; and
    introducing a cooling means into the at least one cooling channel.

11. The method of claim 8, further comprising the step of extending the width of the illumination source by providing a plurality of right and left printed wire board segments joined end to end.

12. The method of claim 8, further comprising the step of finishing a surface of each of the at least two window support means adjacent the plurality of LEDs, the finished surfaces for reflecting illumination from the plurality of LEDs through the window.

13. A web inspection system for detecting defects of a web having a width, the web inspection system comprising:

a plurality of smart cameras for taking images of the web along the width, and for producing defect information;

a computer coupled to the plurality of smart cameras for processing the defect information; and an illumination source for illuminating the web along the width, the illumination source comprising:

an elongate mounting base having a first surface, a second surface, and a longitudinally extending heat sink on said mountain base;

at least one right printed wire board segment mounted on said first surface to extend on one side of said heat sink and at least one left printed wire board segment mounted on said first surface to extend on the opposite side of said heat sink;

a plurality of LEDs mounted at spaced intervals along said heat sink and attached to the at least one right printed wire board segment and the at least one left PWB printed wire board segment for producing illumination;

a support bass attachable to the second surface of the mounting base arid having a first length, the base constructed from a heat transferring material, the support base having a plurality of interior channels extending the first length;

at least two support members attached to a second surface of the mounting base such that the plurality of LEDs are located therebetween, each of the at least two support members comprising a mirrored surface adjacent the plurality of LEDs for directing illumination produced by the LEDs towards the web;

a window attached to the at least two support members; and a housing for enclosing the illumination source, the housing having an open portion aligned with the window for allowing the illumination to be directed towards the web.

14. The web inspection system of claim 13, wherein said LEDs are adhered directly to said heat sink for providing heat transfer from the plurality of LEDs.

15. The web inspection system of claim 13, wherein the housing comprises:

at least two brackets having the first length for enclosing the mounting base, the at least two support members, and at least a portion of the window; and at least two end caps for enclosing first and second ends of the at least two brackets.

16. The web inspection system of claim 13, wherein the plurality of LEDs are attached to the at least one right printed wire board segment and the at least one left printed wire board segment in a parallel series configuration.

17. A linear, modular illumination system for uniform illumination of a target, comprising:

an elongate base support member having a plurality of interior channels extending along its length, the support member having a mounting surface;

at least one lighting segment secured to the mounting surface, the lighting segment comprising an elongate printed wiring board base having a right printed wiring board segment and a left printed wiring board segment, and a plurality of light sources mounted at spaced intervals along the base between the left and right wiring board segments, the light sources being attached to the right and left printed wiring board segments for producing illumination;

at least one of the channels in the base comprising a cooling channel;

a cooling fluid supply connected to said cooling channel to circulate cooling fluid in said channel and cool said light sources;

reflecting means associated with said lighting segment for directing illumination produced by the light sources onto a target; and a housing enclosing the lighting segment and reflecting means, the housing having a window for transmitting illumination from the housing.

18. The system as claimed in claim 17, wherein a plurality of lighting segments are secured end-to-end along said mounting surface of said base support member, the light sources being equally spaced along the entire length of the plurality of lighting segments to produce uniform illumination.

19. The system as claimed in claim 17, further comprising a mounting member with a raised heat sink portion extending along the length of the mounting member and channels running along opposite right and left sides of the heat sink portion, the right printed wiring board segment being seated in the right side channel, the left printed wiring board segment being seated in the left side channel, and the light sources being mounted directly on the raised heat sink portion between the printed writing board segments, whereby heat is dissipated from said right sources by said heat sink portion.

20. The system as claimed in claim 19, wherein the light sources comprise LEDs and the LEDs are secured to the heat sink portion with a heat conducting adhesive.

21. The apparatus as claimed in claim 17, wherein each printed wiring board segment has a first end and a second end, and a plurality of lead pads at equally spaced intervals along the length of the segment, the first lead pad of each segment being at a first spacing from the first end of the segment and the last lead pad of each segment being at a second spacing from the second end of the segment, the first spacing and the second spacing together being equal to the spacing between adjacent lead pads along the segment, whereby the spacing between adjacent end lead pads of two segments when segments are secured together end-to-end is equal to the pad spacing along the length of each segment.

* * * * *